United States Patent [19]

Hueber

[11] Patent Number: 6,078,833
[45] Date of Patent: Jun. 20, 2000

[54] SELF REFERENCING PHOTOSENSOR

[75] Inventor: Dennis M. Hueber, Champaign, Ill.

[73] Assignee: I.S.S. (USA) Inc., Champaign, Ill.

[21] Appl. No.: 09/047,964

[22] Filed: Mar. 25, 1998

[51] Int. Cl.⁷ .................................................. A61B 5/00
[52] U.S. Cl. ...................................... 600/476; 600/310
[58] Field of Search ............................ 600/407, 473, 600/476, 310, 316, 322, 323; 356/39–41, 341

[56] References Cited

U.S. PATENT DOCUMENTS

| | | |
|---|---|---|
| 4,840,485 | 6/1989 | Gratton et al. . |
| 5,057,695 | 10/1991 | Hirao et al. . |
| 5,188,108 | 2/1993 | Secker .................................... 128/633 |

(List continued on next page.)

FOREIGN PATENT DOCUMENTS

| | | |
|---|---|---|
| 0 774 658 A2 | 5/1997 | European Pat. Off. . |
| WO 93/17621 | 9/1993 | WIPO . |
| WO 94/21173 | 9/1994 | WIPO . |
| WO 96/41566 | 12/1996 | WIPO . |

OTHER PUBLICATIONS

Article entitled: LEDs in frequency–domain spectroscopy of tissues by Maria Angela Franceschini et al., Laboratory for Fluorescence Dynamics, University of Illinois at Urbana–Champaign, 300/SPIE vol. 2135, pp. 300–306, Jan. 1994.

Article entitled: Quantitative determination of the absorption spectra of chromophores in strongly scattering media: a light–emitting–diode based technique by Sergio Fantini et al., Applied Optics/ vol. 33, No. 22/ Aug. 1, 1994 pp. 5204–5213.

Article entitled: Rapid Changes of Optical Parameters in the Human Brain During a Tapping Task by Gabriele Gratton et al., Journal of Cognitive Neuroscience 7:4, pp. 446–456, Massachusetts Institute of Technology, 1995.

Article entitled: Possible correlation between blood glucose concentration and the reduced scattering coefficient of tissues in the near infrared, by John S. Maier et al., University of Illinois Optic Letters/vol. 19, No. 24/Dec. 15, 1994 pp. 2062–2064.

Article entitled: Frequency–domain multichannel optical detector for noninvasive tissue spectroscopy and oximetry, by Sergio Fantini, et al., Optical Engineering. Jan. 1995/vol. 34 No. 1, pp. 32–42.

Article entitled: Propagation of photon–density waves in strongly scattering media containing an absorbing semi–infinite plane bounded by a straight edge, by Fishkin et al., University of Illinois Optical Society of America, 1993, vol. 10, No. 1/Jan. 1993/J., pp 127–140.

Article entitled: Quantitative Spectroscopic Determination of Hemoglobin Concentration and Saturation in a Turbid Medium: Analysis of the Effective of Water Absorption, by Franceschini et al., Journal of Biomedical Optics, Apr., 1997, vol. 2 No. 2, pp. 147–153.

Article entitled: "Semi–infinite geometry boundary problem for light migration in highly scattering media: a frequency–domain study in the diffusion approximation", by Fantini et al., J. Opt. Soc. Am. B/vol. 11, No. 10/Oct. 1994, Optical Society of America, pp. 2128–2138.

*Primary Examiner*—Marvin M. Lateef
*Assistant Examiner*—Shawna J. Shaw
*Attorney, Agent, or Firm*—George H. Gerstman; Garrettson Ellis

[57] ABSTRACT

A method and apparatus for determining parameters of a medium, preferably a highly scattering medium such as living tissue. At least two spaced light sources provide light through the tissue or other medium to at least two spaced detectors, with the spacing between the light sources and the detectors being constrained to certain dimensions. The combined data received by such detectors can provide data that is substantially independent of the intensity of the light sources, the sensitivity of the detectors, the coupling efficiency of light from the light sources into the medium, and the coupling efficiency of light from the medium to the detectors. The light from the two sources is of substantially identical wavelength.

22 Claims, 4 Drawing Sheets

U.S. PATENT DOCUMENTS

| | | |
|---|---|---|
| 5,212,386 | 5/1993 | Gratton et al. . |
| 5,323,010 | 6/1994 | Gratton et al. . |
| 5,348,003 | 9/1994 | Caro . |
| 5,492,118 | 2/1996 | Gratton et al. . |
| 5,497,769 | 3/1996 | Gratton et al. . |
| 5,517,987 | 5/1996 | Tsuchiya . |
| 5,564,417 | 10/1996 | Chance . |
| 5,664,574 | 9/1997 | Chance . |

SELF REFERENCING PHOTOSENSOR

BACKGROUND OF THE INVENTION

In Gratton et al. U.S. Pat. Nos. 5,497,769 and 5,492,118, an instrument based on multiple light sources, and using the principles of frequency domain spectroscopy, is described for the noninvasive determination of the light transmission properties of a scattering medium, such as absorption coefficient, reduced scattering coefficient, and index of refraction. By measuring the optical properties of living tissue, the instrument described in U.S. Pat. Nos. 5,497,769 and 5,492,118 can determine the concentrations of such materials as oxyhemoglobin, deoxyhemoglobin, glucose and the like. The principles of frequency spectroscopy are well known, being used in frequency domain fluorometry and/or phosphorimetry, being disclosed for example in Gratton U.S. Pat. No. 4,840,485 et al. and U.S. Pat. Nos. 5,212,386 and 5,323,010, among others.

Such probes typically operate using high frequency, sinusoidally modulated light. Typically, a probe is placed in contact with the surface of the medium to be measured. The average light intensity, the amplitude of the modulation in the light intensity, and the phase of the modulation are measured at multiple source detector separations, allowing the determination of the absorption coefficient, the scattering coefficient and/or the index of refraction of a highly scattering medium such as human or animal tissue. When sources of multiple wavelengths are employed, the concentrations of oxyhemoglobin and deoxyhemoglobin, for example, can be directly measured without the need for any a priori knowledge or estimation of the scattering or reflective properties of the tissue. This is an important advance, in that scattering within tissues varies widely from individual to individual, and among various tissues within an individual. Scattering may even change, over time, within a tissue.

However, the light sources and detector (or detectors) in these prior art techniques must be regularly calibrated with respect to a standard of known light transmission properties. This calibration must be repeated regularly since the intensity and/or phase of a light source may drift due to many factors such as time and temperature, and the sensitivity and phase response of the detector may also drift. Furthermore, this calibration cannot account for possible differences in light coupling efficiency between the standard of known properties and the sample to be measured. Hair, dirt, or the like may effect the efficiency with which the light is transmitted between the probe and the sample. Also, changes in the pressure used to hold the probe against the sample can affect the coupling efficiency of the light into the sample, as well as the coupling efficiency of the exit of the light from the sample to the detector.

In accordance with this invention, a new type of probe is provided, which probe has the advantage of allowing measurements similar to the above to be made without the need for calibration. The intensity of the light sources, the sensitivity of the light detectors, the high frequency phase response of the sources and detectors, the coupling efficiency of any fiber optic light guides present, and the coupling efficiency of light into and out of the highly scattering sample do not need to be known or precisely controlled. Also, correction factors do not need to be found by any calibration performed before or after the measurements, since the probes and the process described herein which are used to make measurements can be rendered independent of the above listed factors, by use of this invention. Thus, data acquired by this invention can be used to calculate the optical properties of samples and, by extension, the concentrations of various substances in the samples, including hemoglobin or glucose in living tissue.

The probes of this invention preferably do not contain moving parts, and are capable of obtaining desired data on a nearly instantaneous basis by irradiation of a highly scattering medium such as human or animal tissue, typically with light in the near infrared region between about 650 nm. and 1000 nm., where the light-absorbance of tissue is low. Such light may travel up to several centimeters through the tissue, providing a spectral window useful for photometric and spectrometric determination of tissue components.

DESCRIPTION OF THE INVENTION

In accordance with this invention, a method of determining parameters of a medium is provided, which comprises the following steps:

One passes a first portion of light from a first light source through the medium to a first detector. Then, one passes a second portion of light from the first light source through the medium to a second detector, which is spaced from the first detector;

One also passes a third portion of light from a second light source through the medium to the second detector identified above. One further passes a fourth portion of light from the second light source through the medium to the first detector.

The distance between the first light source and the first detector and the distance between the second light source and the second detector are substantially equal. The distance between the first light source and the second detector and the distance between the second light source and the first detector are also substantially equal, but different from the previous distance.

The above steps may be performed in any sequential order. The steps involving a single light source may be performed simultaneously.

The data received by the detector in the above steps may then be combined in a manner that is substantially independent of: intensity of the light sources, sensitivity of the detectors, the coupling efficiency of light from the light sources into the medium, and the coupling efficiency of light from the medium to the detectors. From this, one determines a parameter of the medium from the data.

The above light portions are of a substantially identical wavelength, although the method of this invention may be performed again with light portions of differing wavelengths to gain more or better data.

The combined data received by the detectors comprise the intensities of the light portions as a function of the distances through the medium between the detectors and light sources.

The method of this invention may if desired be performed in a manner similar to that described in the above cited patents, particularly U.S. Pat. Nos. 5,497,769 and 5,492,118, particularly in which the combined data is indicative of at least two of the phase, the AC component, and the DC component of signals from the detectors (as defined in those previous patents). Thus, the rate of change of the above components over distance can be used to determine at least two of phase shift, natural logarithm of DC components, and natural logarithm of AC components of the light portions detected by the first and second detectors. From this, a parameter such as the absorption coefficient, scattering coefficient, and/or index of refraction of the medium can be determined, from which concentrations of various components of the medium can be determined and monitored in real time.

Preferably, the method of this invention may be performed by passing modulated portions of light from the respective light sources through a highly scattering medium in the manner described above. The modulated first through fourth portions of light are of substantially the same wavelength, and each are modulated at a first frequency. The first and second light detectors are modulated at a second frequency that is different from the first frequency.

Then, one can preferably derive at a third frequency resultant signals from the light portions detected at the second frequency, the third frequency being the difference between the first frequency and the second frequency and commonly called the "cross correlation frequency". From this, data points can be determined comprising a combination of data from the first and second detectors. The desired parameter of the medium can then be determined from the data points, typically in a manner similar to the description in the previously cited patents.

Particularly, one may utilize in the above method the step of determining a rate of change by distance in at least two of phase shift, the natural log of the D.C. components, and the natural log of the A.C. components detected from the resultant signals derived from the light beams. From this, as stated above, at least one of the absorption coefficient, index of refraction, and the scattering coefficient of the medium can be determined. This makes possible the determination of the absolute concentration in the medium of at least one form of hemoglobin from the absorption coefficient, at typically two wavelengths, for example, using the above method of this invention twice with two different wavelengths of light in accordance with formulas provided in the first two patents cited above. Alternatively, a relative concentration of glucose can be determined in the medium from the scattering coefficient, multiplied by the index of refraction.

By this invention, the step of determining a parameter of the medium from the data can comprise the steps of combining the respective data received from the first and second detectors in a manner that is substantially independent of: intensity of the light sources, sensitivity of the first and second detectors, high frequency phase response of the light sources and detectors, coupling efficiency of light passing from the light sources to the highly scattering medium, and coupling efficiency of light passing from the highly scattering medium to the detectors, with the result that calibration of the light sources and detectors may be rendered unnecessary. The system errors cancel out.

The method of this invention may be used on a repeated basis in a modified way from that described above, sequentially using single members of a plurality of first light sources and sequentially using single members of a plurality of second light sources, for improved data accuracy.

Also, the method of this invention may comprise an added step of respectively passing fifth and sixth portions of light from a third light source respectively to the first and second detectors. The third light source is equidistantly positioned from the first and second detectors, with the result that a reference light source is provided for self-calibration of the detectors. Here also, if desired, one may sequentially use single members of a plurality of such third light sources for improved self-calibration accuracy.

This latter method of using the fifth and sixth light portions represents a second basic embodiment of this invention and may be referred to as the self-referenced absolute probe.

FURTHER DESCRIPTION OF THE INVENTION AND SPECIFIC EMBODIMENTS THEREOF

Figure 1:
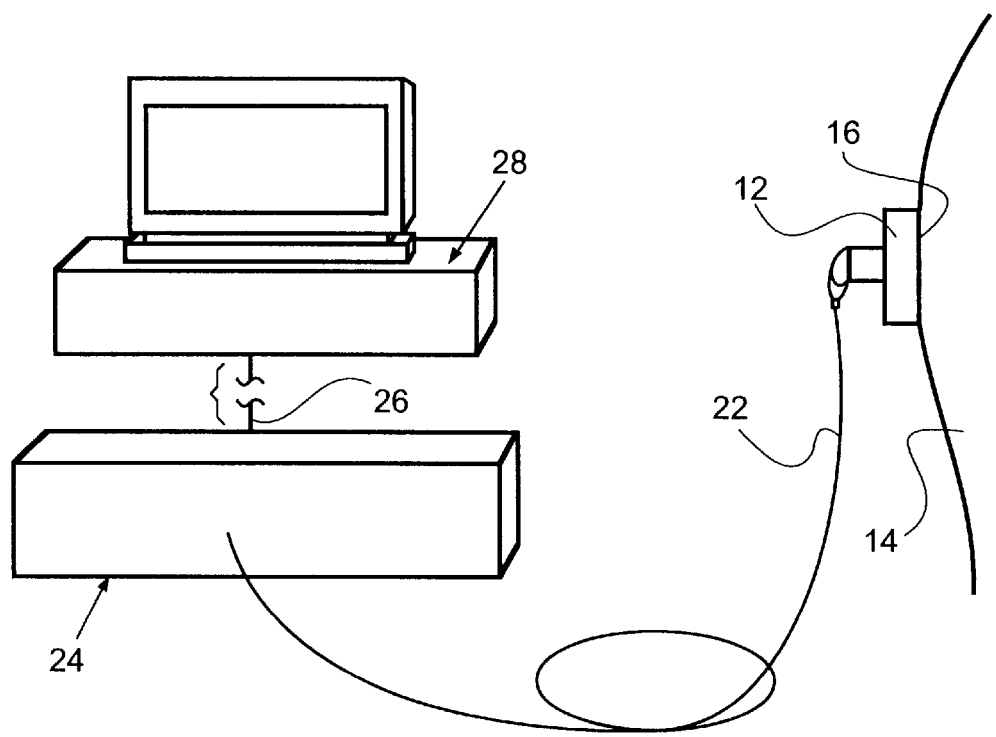
FIG. 1 is a partially schematic view of the apparatus which contains and uses the self-referencing photosensor of this invention to determine parameters of a medium, such as living tissue.

Referring to FIG. 1, an instrument 10 for determining parameters of a medium is disclosed. Particularly, the instrument is for the purpose of monitoring concentrations of hemoglobin, oxyhemoglobin, and/or glucose in the tissue of a living patient. This is accomplished by pressing the face 16 of a probe or rigid housing 12 against the skin of a patient 14, for example the head, thigh, or arm. Also, the probe may be immersed in a liquid. One of the alternative face designs of FIGS. 2–5 may be used, with the face 16 being placed flush against the skin of the patient with firm, gentle pressure.

Figure 2:
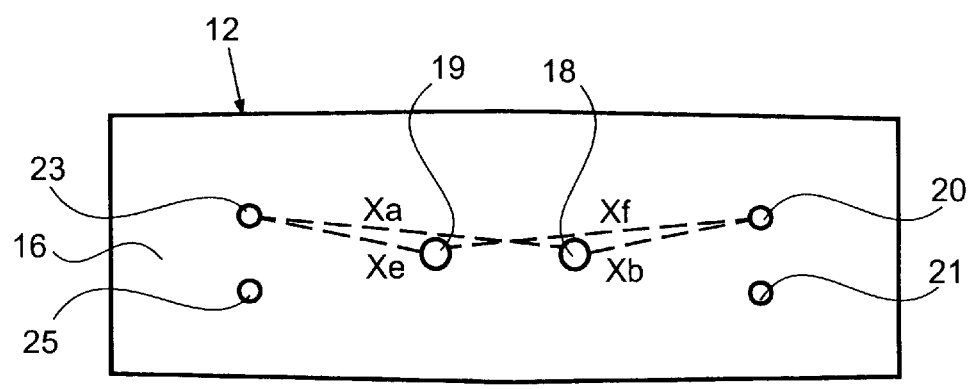
FIG. 2 is a plan view of the face of the probe illustrated in FIG. 1 which rests against the medium in which parameters are being determined, comprising a design for a balanced absolute type probe.

Probe 12 contains in the specific embodiment of FIG. 2 two detectors 18, 19 and four light sources 20, 21, 23, 25, projecting through face 16 of probe 12. Face 16 may be defined by a partition, so that light from light sources 20, 21, 23, 25 may be emitted through the partition to pass through tissue of the patient, and such light passing through the tissue of the patient may be sensed by detectors 18, 19. Detectors 18, 19 and light sources 20, 21, 23, 25 may communicate with wires and/or flexible light guides of cable 22 so that light may pass to the various light sources through cable 22 and signals from detectors 18 may pass through cable 22 to controller 24. Alternatively, light sources may be LEDs mounted in the probe and connected to fine wires, which carry electric potential as governed by controller 24, for selective lighting and extinguishing thereof. Also if desired, a single detector may be used with appropriate fiber optics and other conventional equipment so that light may be detected at different sites or positions on face 16 of probe 12 in alternating manner with the use of a single detector. The detector may reside in controller 24 and communicate with face 16 by a pair of light guides or the like. Additionally, a linear CCD camera may be used in the probe to serve as the detector, connected with fiber optics so that it constitutes an equivalent structure to the separate detectors 18, 19 specifically shown in FIG. 2. An array detector may be used to comprise both of detectors 18, 19. These systems are all encompassed by the term "detector" or "detectors".

Signals from controller 24 may be passed by conductor 26 to an electronic processor such as a computer 28, where the signals may be converted into data and mathematically processed as desired, particularly in the manner described herein.

In addition there may be a system for time sharing the light sources, meaning that each source can be switched on and off, such that only one source is on at any time, and the signal from both detectors is in response to light originating from only one source at any given time. This is provided by conventional circuitry in controller 24. Alternatively and equivalently, some other means of multiplexing the sources may be used, such as chopping or frequency multiplexing.

The need for two sources per wavelength can be reduced if the sources can be optomechanically switched between two or more light guides. Then only one light source per wavelength is required, but two source positions on the probe are still supplied. It is also possible to reduce the number of sources required by using wavelength tunable sources. Also, in theory, one electro optic detector can be switched between two light guides. However, if one detector were time shared in this manner, the measurement of the light reaching the two detector positions could not be made simultaneously. This would be a disadvantage, since the latter device is less sensitive to quick variations in source intensity and other changes.

FIG. 2 shows the face of a probe in accordance with this invention, which probe is of the balanced absolute type. As shown, at least two light sources 20, 23 and two detectors 18, 19 are required. However, it is preferred for a second set of light sources 21, 25 to be provided in a geometry equivalent to that shown.

By this invention, a first portion of light passes from first light source 20 through the tissue medium of the patient 14 to first detector 18, illustrated by line Xb. Simultaneously or sequentially, one passes a second portion of light from first light source through the medium to second detector 19, illustrated by line Xf.

Then, a third portion of light is passed from second light source 23 through the medium to second detector 19, identified as light portion Xe. Simultaneously or sequentially therewith, a fourth portion of light Xa is passed from the second light source 23 through the medium to first detector 18.

Referring to the geometry of the detectors and light sources, the distance between first light source 20 and first detector 18 is substantially equal to the distance between second light source 23 and second detector 19. In other words light portions Xb and Xe are of equal length through the tissue. Also, the distance between first light source 20 and second detector 19 is substantially equal to the distance between second light source 23 and first detector 18. In other words the lengths of light portions Xa and Xf through the tissue are substantially equal, and different from the former distance.

Light sources 20 and 23 are of substantially the same wavelength. Light sources 21 and 25 are optionally provided to permit the same method to be performed at a different wavelength, which makes possible in some circumstances the quantitative determination of components of the tissue medium 14, such as oxyhemoglobin and/or deoxyhemoglobin. Thus, if desired, the method described above is performed with the light sources 21, 25 of the same wavelength, but differing from the wavelength of light sources 20, 23, using the same detectors 18, 19. It can be seen that the same distance constraints between the light sources and the detectors applies for sources 21, 25 as is found for sources 20, 23. Additional light source pairs of additional wavelengths may be added if desired.

To further illustrate the invention, some theoretical background follows:

As light travels outwardly from a light source in a homogeneous highly scattering medium, the radiant energy density, U, observed (or measured) at a point in the medium decreases exponentially with increasing distance from the source as a function of distance between the observed point and the source. The rate of change in U with distance depends on the optical properties of the medium. If the radiant intensity of the light source is sinusoidally modulated, a "photon density wave" can be said to propagate through the medium outward from the source. The variation in time, t, of radiant energy density, u, at any point, x, in the medium can be described by the wave equation, $$U(t) = U_{AC}(x)\sin(2\pi ft + \Phi_u) + U_x(x)$$

$U_{AC}$ is the amplitude of the modulation, f is the frequency of the modulation, $\Phi_U$ is the phase, and $U_{DC}$ is the average radiant energy density. Both $U_{AC}$ and $U_{DC}$ decrease exponentially as a function of the distance between the observed point and the source. However, $U_{AC}$ decreases more quickly than does $U_{DC}$.

While a photon density wave travels with a constant frequency and speed, the speed of the photon density wave is slower than the speed of light in the medium. The phase (or phase shift) at a fixed time, increases linearly with distance according to the speed of the photon density wave.

The rate of change in $U_{AC}$, $U_{DC}$ and $\Phi_U$ with distance all depend on the optical properties of the medium. By measuring the changes in $U_{AC}$, $U_{DC}$ and $\Phi_U$, information about the optical properties of the medium can be obtained. Three of these properties are the absorption coefficient $\mu_a$, reduced scattering coefficient, $\mu'_s$, and index of refraction, $\eta$. The absorption coefficient is a measure of the amount of absorption in the material, $\mu'_s$ is a measure of the amount of scattering, and $\eta$ is a measure of the speed of light in the medium. Scattering and absorption in a material vary with the wavelength of the light. So to measure $\mu_a$, and $\mu'_s$, light sources that emit in a narrow wavelength band (or detectors that detect only a narrow wavelength band) are used.

According to "photon diffusion theory", $\mu_a$ and $\mu'_s$ or $\eta$ can be estimated in a highly scattering medium by measuring the change in $U_{AC}$, $U_{DC}$ and/or $\Phi_U$ with distance. The mathematics behind this assertion have been previously discussed in U.S. Pat. Nos. 5,497,769 and 5,492,118, for the case of a probe placed in contact with the surface of a uniform medium. Briefly, if the quantities ln $(U_{AC}d^2)$, ln (natural log) $(U_{DC}d^2)$, and $\Phi_U$ are plotted versus d, where d is the distance between the source and detector, each would give a straight line and the slope of these lines can be used to calculate the values of $\mu_a/\eta$ and $\eta\mu'_s$, or if $\eta$ is known, $\mu_a$ and $\mu'_s$. It is necessary to determine two of these three slopes, usually either the change in ln $(U_{AC}d^2)$ or ln $(U_{DC}d^2)$ and the change $\Phi_U$ with d is used, since the use of the first two slopes only requires great precision in measurement. Similar mathematical methods suitable for surface measurements and measurement using a probe immersed in the sample have been described, for example see Fishkin and Gratton "Propagation of Photon-density Waves in Strongly Scattering Media Containing an Absorbing Semi-infinite Plane Bounded by a Straight Edge.", J. Opt. Soc. Am. A, Vol. 10, No. 1, pp 127–140.

In regard to the present invention, it should be stressed that these quantities define straight lines with d, so the slope of the line is the rate of change with d between any two points. Therefore, the $\mu_a$ and $\mu'_s$ of a homogenous highly scattering medium can be found knowing only the ratio of the average $U_{DC}$ (or $U_{AC}$) at two, or more, distances from a point source, the phase at two, or more, distances from the source, and $\eta$ in the medium. The values of $\eta\mu'_s$ and $\mu_a/\eta$ can be independently found, but $\eta$ can not be separated from $\mu'_s$ and $\mu_a$ by the measurements alone. Fortunately, $\eta$ can be determined in tissues by other methods (see for example Bolin et al. "Refractive Index of Some Mammalian Tissues using a Fiber Optic Cladding Method", Applied Optics, Vol. 28, No. 12, pp 2297–2303, 1989.). Also, while η varies with wavelength, it is nearly constant in many materials over a small wavelength range, including tissues.

The absorption coefficient of a sample in an important property because; if the number of absorbing components in the medium is known; and if $\mu_a$ is known at a number of wavelengths at least equal to the number of absorbing components; and if the extinction coefficients of each absorbing component is unequal at the measured wavelengths; the concentration of the absorbers can be determined. For the simple case of two absorbers A and B and $\mu_a$ measured at two wavelengths:

$$[A] = \frac{\mu_{a,\lambda 1}\epsilon_{B,\lambda 2} - \mu_{a,\lambda 2}\epsilon_{B,\lambda 1}}{\epsilon_{A,\lambda 1}\epsilon_{B,\lambda 2} - \epsilon_{A,\lambda 2}\epsilon_{B,\lambda 1}}$$

$$[B] = \frac{\mu_{a,\lambda 2}\epsilon_{A,\lambda 1} - \mu_{a,\lambda 1}\epsilon_{A,\lambda 2}}{\epsilon_{A,\lambda 1}\epsilon_{B,\lambda 2} - \epsilon_{A,\lambda 2}\epsilon_{B,\lambda 1}}$$

where [A] is the concentration of one component and [B] is the concentration of the other. The extinction coefficient of component A, at wavelength λ1, is given by $\epsilon_{A,\lambda 1}$, and the extinction coefficient of component A, at wavelength λ2, is given by $\epsilon_{A,\lambda 2}$ etc.

The function symbolism, $U_{DC}(x)$, is used herein to represent the average U within a sample, where x is the distance between the entry point of the light into the sample and the observed point, or the "source detector separation". If the wavelength of the source must be specified, it may be done so with a subscript λ, i.e. $U_{DC}(x)\lambda$. The ratio of $U_{DC}(x)\lambda$ at two separations and λ would be given by, $$\frac{U_{DC}(x_1)\lambda}{U_{DC}(x_2)\lambda}$$

where $x_1$ and $x_2$ are the two distances, or, $U_{DC}(x_1)\lambda/U_{DC}(x_2)\lambda$. Similarly, the amplitude of the modulation in the radiant energy density will be denoted as $U_{AC}(x)$ or $U_{AC}(x)\lambda$, and the ratio at two distances as $U_{AC}(x_1)\lambda/U_{AC}(x_2)\lambda$. The phase of the photon density wave at a given distance x, will be written as $\Phi_U(x)$ again with a subscript λ when the wavelength is specified. The difference between the phase at two positions would then be $\Phi_U(x_1)\lambda - \Phi_U(x_2)\lambda$. The symbols DC and AC will be used to represent the dc and ac components of a photoelectric detector signals, and P for the phase of the signals.

It should be noted that $U_{DC}(x_1)\lambda/U_{DC}(x_2)\lambda$ is equal to the ratio of any values directly proportional to $U_{DC}(x_1)\lambda$ and $U_{DC}(x_2)\lambda$, such as the average radiant flux at a detector or the electronic signal from a detector (the DC part of the signal). Similarly, $U_{AC}(x_1)\lambda/U_{AC}(X_2)\lambda$ is equal to the ratio of any values directly proportional to $U_{AC}(x_1)\lambda$ and $U_{AC}(x_2)\lambda$, such as the AC part of the signal. Indeed, if two linear detectors of exactly equal characteristics and optical paths could be used to simultaneously monitor the light in the medium at two distance s ($x_1$ and $x_2$) from a single light source of wavelength λ, the ratio of $U_{DC}(x_1)\lambda/U_{DC}(x_2)\lambda$ could be directly found from the ratio of $DC(x_1,d_1)\lambda/DC(x_2,d_2)\lambda$ (where $d_1$ and $d_2$ could indicate detectors 18 and 19). Also, the value of $U_{AC}(x_1)\lambda/U_{AC}(x_2)\lambda$ would be equal to $AC(x_1,d_1)\lambda/AC(x_2,d_2)\lambda$, and $\Phi_U(x_1)\lambda - \Phi_U(x_2)\lambda$ would be equal to $P(x_1,d_1)\lambda - P(x_2,d_2)\lambda$.

However, it is not practical to use two exactly matched high-sensitivity, high-speed, detectors that are coupled to a sample with two identical optical paths. The probes described here can be used to measure $U_{DC}(x_1)\lambda/U_{DC}(x_2)\lambda$, $U_{AC}(x_1)\lambda/U_{AC}(x_2)\lambda$ and $\Phi_U(x_1)\lambda - \Phi_U(x_2)\lambda$ in a homogenous scattering even if the intensity of the sources are unknown and unequal, and even if the sensitivities and phase response of the detectors are unknown and unequal. It is equally impractical to use two perfectly similar sources (and similar source optical paths). Various mechanical solutions could be proposed, in which the detector positions and/or source position is changed be means of a moving mirror or other device. However, the probes described here require no moving parts, and little additional complication.

FIG. 2 illustrates a balanced absolute probe, which provides quantative reading without calibration, being independent of errors caused by the system variables described above. Specifically, several prototype absolute probes have been used with an ISS Dual Channel Oximeter. The ISS Oximeter time-shared up to sixteen modulated laser diodes, and has two photomultiplier (PM) detectors, all being coupled to flexible fiber optic light guides. The timing of the source switching is controlled by a personal computer 28, and an analog-to-digital converter is used to measure the signal from two photomultipliers.

In the prototype probes, light guides were used. Therefore references to light sources herein should be understood to refer to the points at which light is emitted from the probe and into the sample. Also a fiber optic light guide was used to connect the detectors 18, 19 to the probe, so the term "detector" should be understood to refer to the position on probe face 14 from which the light striking the detector is collected, and the "source/detector separation" is the distance between the points from which light is emitted by the probe and collected by the probe.

Figure 3:
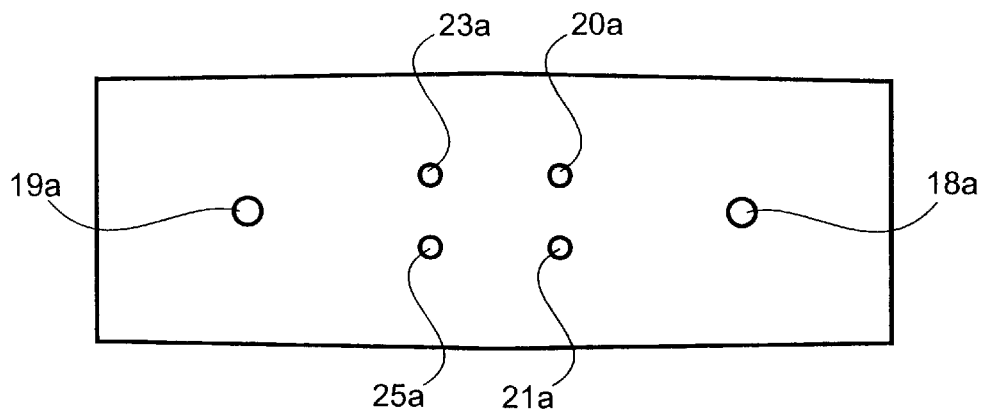
FIG. 3 is an alternative design for the probe face of FIG. 1.

Referring to FIG. 3, an alternate version of the balanced, absolute probe is disclosed, being similar in function to the arrangement of FIG. 2, but with detectors 18a, 19a being positioned on the outside of a group of light sources 20a, 21a, 23a, 25a. It can be seen that the positioning constraints described above apply in this embodiment as well as the embodiment of FIG. 2, in that the distance between first light source 20a and first detector 18a is the same as the distance between second light source 23a and second detector 19a. Also, as before, the distance between first light source 20a and second detector 19a is substantially the same as the distance between second light source 23a and first detector 18a.

Added light sources 21a, 25a are present for the purpose similar to the use of added light sources 21, 25 in the embodiment of FIG. 2, with these latter two light sources providing light of identical wavelength different from the identical wavelength of the first and second light sources 20a, 23a.

Thus, in use, each of the light sources of the arrangements of FIGS. 2 and 3 is switched on for a brief period of time (from milliseconds to seconds) and the corresponding signals from both detectors are measured simultaneously. Otherwise, the measurement of the detectors may be sequential if desired, and each of the light sources is turned on and off sequentially so that the detectors are detecting light from only one light source. The symmetry of the above light source arrangement allows the calculation of an average $U_{DC}(x_2)\lambda/U_{DC}(x_1)\lambda$; $U_{AC}(x_2)\lambda/U_{AC}(x_1)\lambda$; $\Phi_u(x_2)\lambda - \Phi_u(x_1)\lambda$ without calibration, where $x_1$ and $x_2$ are the two source-detector separations, for example Xa and Xb for one source-detector separation and Xe, Xf for the other source-detector separation (FIG. 2).

To show this mathematically, first we note that when a first source (e.g. source 20) is on $U_{DC}(x_1)\lambda$ and $U_{DC}(x_2)\lambda$ could be found from two relationships if the sensitivity factor for the detectors and intensity factors for the sources were known, $$U_{DC}(x_1)\lambda = I_{s1}U'_{DC,s1}X_{d1,\lambda}S_{d1,\lambda}DC(x_1,s_1,d_1) \text{ and} \quad [1]$$

$$U_{DC}(x_2)\lambda = I_{s1}U'_{DC,s1}X_{d2,\lambda}S_{d2,\lambda}DC(x_2,s_1,d_2) \quad [2]$$

The indicators $d_1$ and $d_2$ refer to the detectors in the system, such as detectors 18, 19 in FIG. 2 and corresponding detectors in other figures. Indicators $s_1$, $s_2$ refer to the first and second light sources such as sources 20, 23 in FIG. 2 and corresponding sources in other figures. $DC(x_a,s_b,d_c)$ is the average signal from detector c due to source b, which is at distance $x_a$. $X_{d1,\lambda}$ is the sensitivity of the detector c, in units of volts (or current) per unit photon density. $U'_{DC,sb}$ is the intensity of source b. $S_{dc,\lambda}$ is the sensitivity loss factor for detector c (including all proportional losses) at the wavelength of sources 1 and 2 ($\lambda$). $I_{sb}$ is the intensity loss factor (including all proportional losses) for source b. The intensity loss factors, I, detector loss factors, S, intensities, U', and sensitivities, X, are unknown.

Similarly, when the second light source $s_2$ (e.g. source 23) is on, $$U_{DC}(x_1)\lambda = I_{s2}U'_{DC,s2}S_{d2,\lambda}X_{d2,\lambda}DC(x_1,s_2,d_2) \text{ and} \quad [3]$$

$$U_{DC}(x_2)\lambda = I_{s2}U'_{DC,s2}S_{d1,\lambda}X_{d1,\lambda}DC(x_2,s_2,d_1) \quad [4]$$

Next, by trivial manipulation, we note that, $$\ln\left[\frac{U_{DC}(x_2)_\lambda}{U_{DC}(x_1)_\lambda}\right] = \ln\sqrt{\frac{U_{DC}(x_2)_\lambda^2}{U_{DC}(x_1)_\lambda^2}} \quad [5]$$

$$= 1/2 \ln\left[\frac{U_{DC}(x_2)_\lambda U_{DC}(x_2)_\lambda}{U_{DC}(x_1)_\lambda U_{DC}(x_1)_\lambda}\right]$$

By substituting the expressions for $U_{DC}(x_1)\lambda$ and $U_{DC}(x_2)\lambda$ in equations [1]–[4] into the final term of equation [5] we have, $$\ln\frac{U_{DC}(x_2)_\lambda}{U_{DC}(x_1)_\lambda} \cong 2 \ln\frac{DC(x_2,s_1,d_2)_\lambda DC(x_2,s_2,d_1)_\lambda}{DC(x_1,s_1,d_1)_\lambda DC(x_1,s_2,d_2)_\lambda} \text{ or} \quad [6]$$

$$\frac{U_{DC}(x_1)_\lambda}{U_{DC}(x_2)_\lambda} \cong \sqrt{\frac{DC(x_2,s_1,d_2)_\lambda DC(x_2,s_2,d_1)_\lambda}{DC(x_1,s_1,d_1)_\lambda DC(x_1,s_2,d_2)_\lambda}} \quad [7]$$

Where all of the I and S factors have cancelled. (The $\equiv$ symbol is used above to emphasize that there is always some error in measurement.)

By analogous argument, we can show that, $$\ln\frac{U_{AC}(x_2)_\lambda}{U_{AC}(x_1)_\lambda} \cong 1/2 \ln\frac{AC(x_2,s_1,d_2)_\lambda AC(x_2,s_2,d_1)_\lambda}{AC(x_1,s_1,d_1)_\lambda AC(x_1,s_2,d_2)_\lambda} \text{ or} \quad [8]$$

$$\frac{U_{AC}(x_2)_\lambda}{U_{AC}(x_1)_\lambda} \cong \frac{AC(x_2,s_1,d_2)_\lambda AC(x_2,s_2,d_1)_\lambda}{AC(x_1,s_1,d_1)_\lambda AC(x_1,s_2,d_2)_\lambda} \quad [9]$$

For phase, the mathematics is slightly different. First we note that if the phase delays introduced in the device where known, the phase of the photon density wave at the two distances could be found while source 1 is on from, $$\Phi(x_1)\lambda = P(x_1,s_1,d_1) + q_{d1,\lambda} + w_{a1,\lambda} \text{ and } \Phi(x_2)\lambda = P(x_2,s_1,d_2) + q_{d2,\lambda} + w_{s1,\lambda'} \quad [10],[11]$$

where $P(x_a,s_b,d_c)$ is the measured phase on detector c due to the light from source b (which traveled distance $x_a$). The phase delay's of the detectors (electronic and optical) is given by $q_{d1,\lambda}$ and $q_{d2,\lambda}$, and $w_{s1,\lambda}$ and $w_{s2,\lambda}$ are the phase delays for the sources (electronic and optical).

When the second light source is on we find that, $$\Phi(x_2)\lambda = P(x_2,s_2,d_1) + q_{d1,\lambda} + w_{s2,\lambda} \text{ and } \Phi(x_1)\lambda = P(x_1,s_2,d_2) + q_{d2,\lambda} + w_{s2,\lambda}. \quad [12],[13]$$

Next we note that, $$\Phi_U(x_2)_\lambda - \Phi_U(x_1)_\lambda = \frac{2[\Phi_U(x_2)_\lambda - \Phi_U(x_1)_\lambda]}{2} \quad [14]$$

$$= \frac{\Phi_U(x_2)_\lambda + \Phi_U(x_2)_\lambda - \Phi_U(x_1)_\lambda - \Phi_U(x_1)_\lambda}{2}$$

By substituting the expressions for $\Phi_U(x_1)$ and $\Phi_U(x_2)$ from [10]–[13] into the final term of [14] we have, $$\Phi_U(x_1)\lambda - \Phi_U(x_2)\lambda \cong$$

$$\Phi_U(x_1)_\lambda - \Phi_U(x_2)_\lambda \cong$$

$$\frac{[P(x_1,s_1,d_1) + P(x_1,s_2,d_2) - P(x_2,s_1,d_2) - P(x_2,s_2,d_1)]}{2}$$

Additional wavelengths can be added to a balanced absolute probe by tuning the sources to another wavelength, if they are tunable or simply adding more source positions 21, 25 to the probe. Each set of additional light source positions must hold the same symmetry described above with respect to the two detector positions, but do not necessarily have to define the same two source detector separations. While there must be at least two light sources per wavelength, there may also be more than two, each pair holding the same symmetry with the detectors.

THE SELF-REFERENCING ABSOLUTE PROBE

Figure 4:
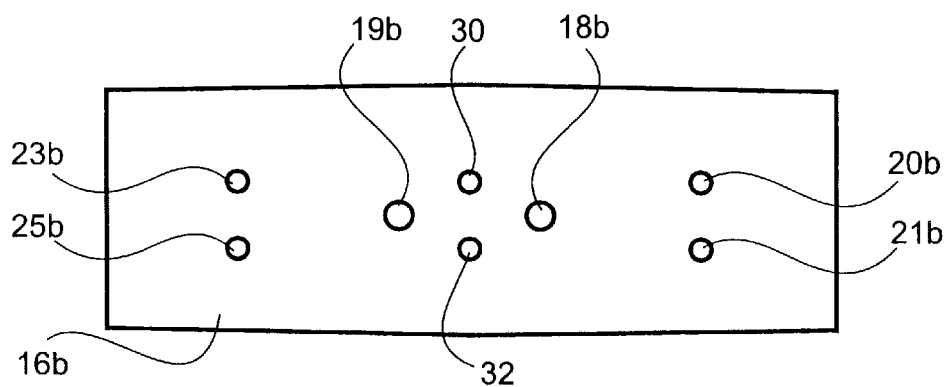
FIG. 4 is an alternate design for the probe face of FIG. 1, comprising a self-referencing absolute type probe.

Referring to FIG. 4, a modification of the scheme illustrated particularly in FIGS. 2 and 3 is shown.

FIG. 4 shows the face 16b of a probe 12, which probe is similar to function to the previous embodiments, but which contains a self-referencing function. Specifically, the probe face of FIG. 4 is similar to the embodiment of FIG. 2 in that it carries four light sources 20b, 21b, 23b, 25b in a rectangular arrangement that is similar to the corresponding light sources of FIG. 2. Also, probe face 16b carries a pair of photodetectors 18b, 19b which are preferably positioned in the same position as the corresponding photodetectors of the FIG. 2 embodiment. However, this system is more tolerant of variable and asymmetric spacing arrangements than the previous embodiments.

By this invention, at least one added reference light source 30 is provided, as well as preferably a second reference light source 32. Reference light source 30 emits light of the wavelength of light sources 20b, 23b, while reference light source 32 emits light of the wavelength of light sources 21b, 25b. Reference source 30 is positioned equidistantly from the respective detectors 18b, 19b. The other light sources 20b, 23b that work with reference light source 30 are preferably confined to the symmetry described above, but the specific light source detector distances may vary. The same applies to the relationship between reference light source 32 and the other light sources 21b, 25b with which it works.

Each of the light sources is switched on sequentially for a brief period. The cycle may be repeated continuously if desired.

Reference light sources 30, 32 can be used to determine detector sensitivity and phase correction factors. These sensitivity and phase response correction factors, which may be dynamically measured, can then be applied to the signals detected from the respective light sources 20b, 23b (and corresponding light sources 21b, 25b) while each of the detectors 18b, 19b is on. For example, first reference light source 30 may be turned on, and the ratio of the average signal magnitude from detectors 18b and 19b can be recorded. Then, reference light source 30 can be turned off, and measurement light source 20b can be turned on, with the average signal magnitude of detectors 18b, 19b being recorded. Next, the value measured at detector 19b in this step is multiplied by the recorded ratio of the response of detector 19b to the response of detector 18b to light from reference light source 30. Thus a correction can be applied that eliminates error due to different sensitivities of the respective detectors 18b, 19b. Then, measurement light source 23b can be treated similarly to source 20b as above for further calibration.

Similarly, the amplitude of the modulation of the light provided to the system and the phase can be corrected, except that an additive correction factor may be used for the phase. The correction factors are given by the following:

$$C_{DC,\lambda} = \frac{DC(x_R, s_R, d_1)_\lambda}{DC(x_R, s_R, d_2)_\lambda} \quad [16]$$

$$C_{AC,\lambda} = \frac{AC(x_R, s_R, d_1)_\lambda}{AC(x_R, s_R, d_2)_\lambda}, \text{ and} \quad [17]$$

$$C_{\Phi,\lambda} = P(x_R, s_R, d_1)\lambda - P(x_R, s_R, d_2)\lambda, \quad [18]$$

where $C_{DC,\lambda}$, and $C_{\Phi,\lambda}$ are the correction factors for DC(x, s,d$_2$)$\lambda$, AC(x,s,d$_2$)$\lambda$ and $\Phi_s$(x,s,d$_2$),$\lambda$, and s$_R$ and x$_R$ represent the reference source 30 or 32 and the reference source-detector separation. The values of UDC(x$_1$)$\lambda$/UDC(x$_2$)$\lambda$, UDC(x$_1$)$\lambda$/UDC(x$_2$)$\lambda$ and $\Phi_U$(x$_1$)$\lambda$-$\Phi_U$(x$_2$)$\lambda$ can be found from, $$\frac{U_{DC}(x_1)_\lambda}{U_{DC}(x_2)_\lambda} \cong \frac{DC(x_1, s_1, d_1)_\lambda}{C_{DC,\lambda} DC(x_2, s_1, d_2)_\lambda} \quad [19]$$

$$\cong \frac{C_{DC,\lambda} DC(x_1, s_2, d_2)_\lambda}{DC(x_2, s_2, d_1)_\lambda}$$

$$\frac{U_{AC}(x_1)_\lambda}{U_{AC}(x_2)_\lambda} \cong \frac{AC(x_1, s_1, d_1)_\lambda}{C_{AC,\lambda} AC(x_2, s_1, d_2)_\lambda} \quad [20]$$

$$\cong \frac{C_{AC,\lambda} AC(x_1, s_2, d_2)_\lambda}{AC(x_2, s_2, d_1)_\lambda} \quad \text{and}$$

$$\Phi_U(x_1)\lambda - \Phi_U(x_2)\lambda \cong P(x_1, s_1, d_1)\lambda - (P(x_2, s_1, d_2)\lambda - C_{\Phi,\lambda}) \cong P(x_2, s_1, d_2)\lambda - C_{\Phi,\lambda} - P(x_1, s_1, d_2)\lambda \quad [21]$$

As can be seen from these equations, the presence of multiple light sources provides a redundant measurement. The multiple results can be averaged. It is also possible to have only two source positions per wavelength, one measurement and one reference.

As FIG. 4 suggests, one probe may fit both basic design criteria, balanced absolute and self-referencing; it may have the symmetry described above and a third (per wavelength) "reference" source. In this case, this symmetry is preferred since then either set of equations may be used, or both may be used and the answers compared as a check of sample homogeneity.

In use, either type of absolute probe is pressed firmly against the material to be measured, or if the sample is fluid, the probe may be immersed into the sample. A cycle of turning each source on in turn is established and repeated indefinitely. The signal from both detectors is monitored, and the AC, DC and $\Phi$ associated with each source's "on" period is measured. The computer may be used to calculate the values of $U_{DC}(x_1)\lambda/U_{DC}(x_2)\lambda$, $U_{AC}(x_1)\lambda/U_{AC}(x_2)\lambda$, $\Phi(x_1)\lambda-\Phi(x_2)\lambda, \mu_a, \mu'_s$, etc. at each wavelength. The results may be displayed or stored by the computer. The results of several cycles may be averaged for improved signal-to-noise in the measurements.

Thus it can be seen that the probe of FIG. 4 may be used to make absolute (self-calibrated) measurements as described above, or they may be used to measure the initial (average) optical properties, and then used with only one light source per wavelength active. The initial optical properties of the medium being examined and the measured values may be used to calculate "correction factors" to equalize the response of the respective two detectors 18b, 19b. Further measurements may then be made using only one source position per wavelength, i.e. only one of light sources 20b, 23b and only one of light sources 21b 25b. If the light sources are time multiplexed, this can allow more rapid measurement of changes in the optical properties of a sample, for real time measurement of the optical properties.

Figure 5:
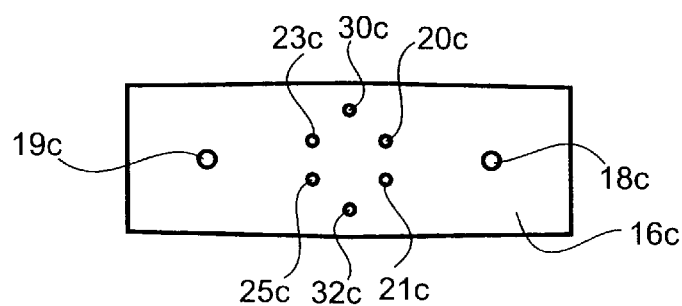
FIG. 5 is another embodiment of a self-referencing absolute probe face.

Referring to FIG. 5, a face 16c of probe 12 is shown in a different embodiment, which embodiment is equivalent to the embodiment of FIG. 4.

In this latter embodiment, the first and second detectors 18c, 19c are positioned outside of the respective light sources used herein. Light sources 20c, 21c, for differing wavelengths, are positioned as shown along with light sources 23c, 25c, being equivalent to their counterparts of same number in FIG. 4. The spatial relationship of these four light sources to the first and second detectors 18c, 19c is preferably the same as found in the embodiment of FIG. 3, but with the two reference sources 30c and 32c added. Reference sources 30c, 32c are positioned equidistantly between detectors 18c, 19c, to function in the manner described with respect to the corresponding reference light sources 30, 32 in the embodiment of FIG. 4.

Example

Several prototype probes of the balanced absolute and the self-referencing type (respectively of FIGS. 2 and 4) have been fabricated and used to measure samples with optical properties which were previously determined by single source, single detector measurements. The light sources and detectors used comprised an ISS Dual Channel Oximeter, similar to the design disclosed in the previously cited U.S. Pat. No. 5,497,769, having sets of multiple-distance light sources at two wavelengths and detectors coupled to fiber optic light guides. The instrument uses a heterodyne and digital Fourier transform approach as described in the patent cited immediately above to measure the relative amplitude and phase of the modulated light that strikes the respective detectors of the modified head 12 of this invention, used with the device of the previously cited patent. The light sources are amplitude modulated diode lasers, while the detectors were sensitivity modulated photomultiplier tubes (PMTs). The PMTs are modulated at a frequency slightly different from the principal frequency of 110 MHz which is used to modulate the laser diodes. Thus, the detector produces a signal at a cross correlation frequency which is equal to the difference between the principal modulation frequency and the detector modulation frequency. This cross-correlation frequency may be typically up to about 10 KHz.

The average detector signal and amplitude of the modulation at the cross correlation frequency is proportional to the average intensity of the light striking the detector and the amplitude of the modulation in the intensity of the light. The phase of the detector's cross-correlation frequency signal is equal to the phase of the modulation in the light at the principal frequency. The signal from both detectors is sampled by an analog-to-digital converter in a personal computer. A Fourier transform algorithm of conventional type is used to calculate the amplitude of the modulation at the cross-correlation frequency (AC), the phase of the signal (P), and the zero frequency amplitude (DC).

The medium upon which tests were performed comprised an aqueous suspension containing Liposyn III fat emulsion (Abbott Laboratories) used to provide high scattering to the medium, and india ink as an absorber, placed in a plastic, cylindrical container of roughly fourteen inch diameter and seven inch height, holding more than six liters of such media. Thus, such a media was effectively infinite with respect to the light sources and detectors when positioned near the center of the container, and effectively semi-infinite, with a single plane boundary, with respect to a light source and a detector held in contact with the top surface of the medium. Various quantities of Liposyn were added to the mixture to get a variation of solids content for different tests, and the optical properties of each mixture were measured using, respectively, a probe of the design of FIG. 2.

The probe of the balanced absolute design of FIG. 2 was operated with two light 20, 23 sources of 830 nm, two light sources 21, 25 of 750 nm, and two detectors 18, 19. The distance between detectors 18,19 was 1.4 cm. The shorter source-detector separation was 1.5 cm. The longer source-detector separation was 2.9 cm.

The probe was positioned on the Liposyn aqueous medium, with the tips of light sources 20, 21, 23, 25 (which were light guides) being held about 1 mm below the surface of the aqueous medium. Each light source was left on for forty milliseconds, so that a complete illumination cycle of all four sources lasted 0.32 second, there being some dead time between the illumination of the various light sources. The results of many cycles were averaged for at least 10 seconds, and the averaged results were used to calculate optical parameters. The calculations were performed (as presented in S. Fantini, M. Franceschini and E. Gratton "Semi-Infite-Geometry Boundary Problem for Light Migration in Highly Scattering Media: A Frequency-Domain Study in the Diffusion Approximation." Journal of the Optical Society of America part B, Volume 11, Number 10, October 1994, ppg 2123–2128, or U.S. Pat. No. 5,497,769) for a semi-infinite medium.

A reference probe was used to check the data obtained on the absolute probe of FIG. 2. The reference probe comprised a single light source fiber and a single light detection fiber. The light source was switched between a 750 nm laser diode and an 840 um laser diode during the procedure. The distal ends of the light source fibers were positioned near the center of the container and submerged in the aqueous Liposyn media. The distance between the fibers was precisely adjustable by a computer controlled translation stage. The source-detector separation was changed to at least four positions for each measurement cycle, the average AC, DC, and Phase shift of the signal being recorded at each position for a few seconds. Thus all readings came from a single light source and light detector. The cycle was repeated at least five times to ensure that changes in source intensity and other instrumental drifts did not effect the results. The average optical parameters were calculated based on the results using the theory presented in the previous citation for photon diffusion in an infinite medium.

The absolute probe of FIG. 2 and the reference probe used as a control were tested at wavelengths of 750 nm and 840 nm.

Figure 6:
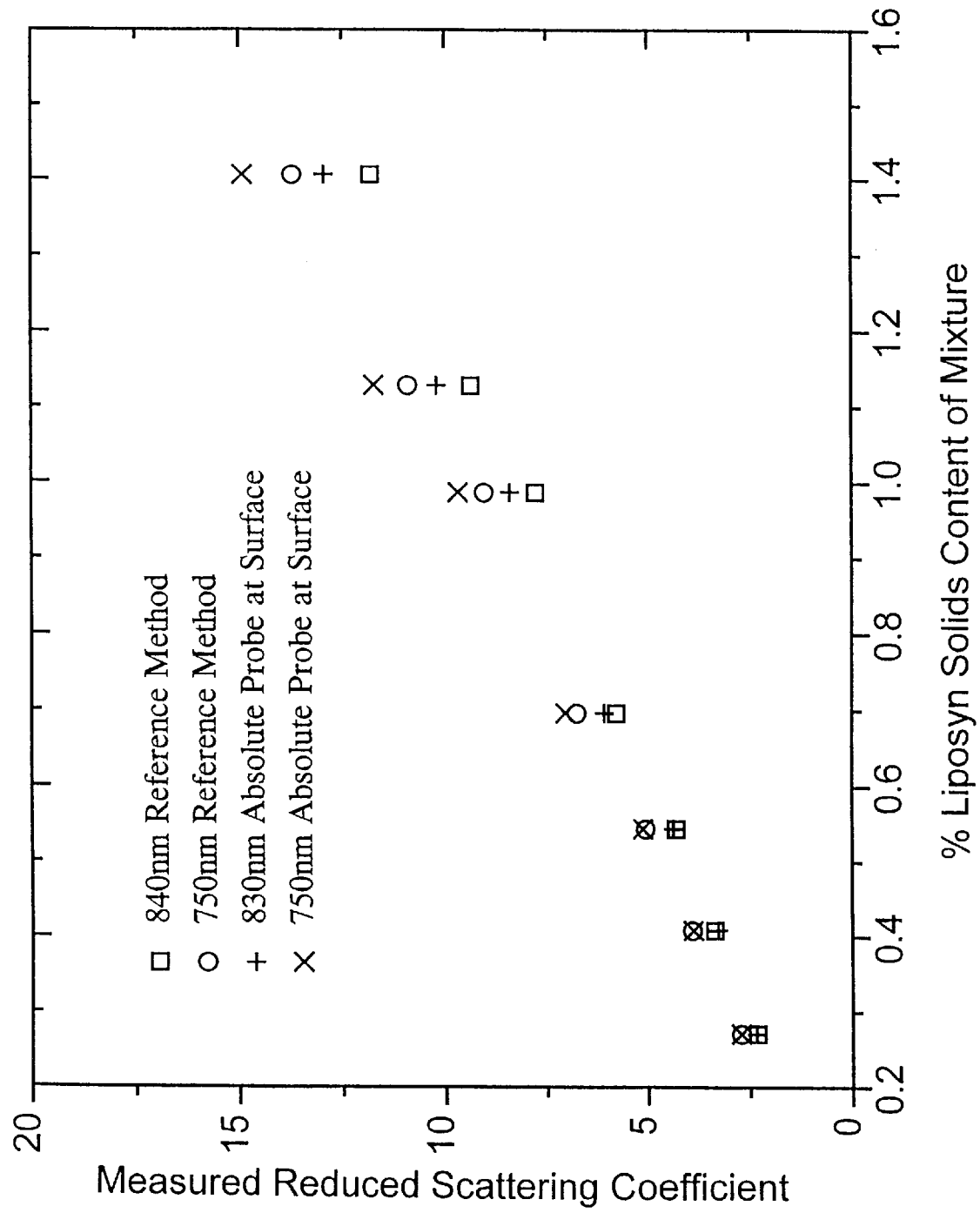
FIG. 6 is a graph showing measurement of the reduced scattering coefficient at varying degrees of scattering.

FIG. 6 shows the measured and computed reduced scattering coefficient determined at the two wavelengths by each probe system at varying concentrations of Liposyn in the mixture, which creates differing degrees of light scattering. The content of the ink in the system remained substantially constant as only relatively minor amounts of Liposyn were added to achieve the differing solids contents.

It can be seen that under relatively low scattering conditions, the new absolute probe of FIG. 2 gives results that are experimentally identical to the reference method used as a control. At higher levels of scattering, the probe of FIG. 2 gives somewhat larger values than the reference probe method, but the results still demonstrate that the reduced scattering coefficient can be estimated to within 10 percent over a large range of scattering at these higher scattering levels, without the need for instrument calibration.

Figure 7:
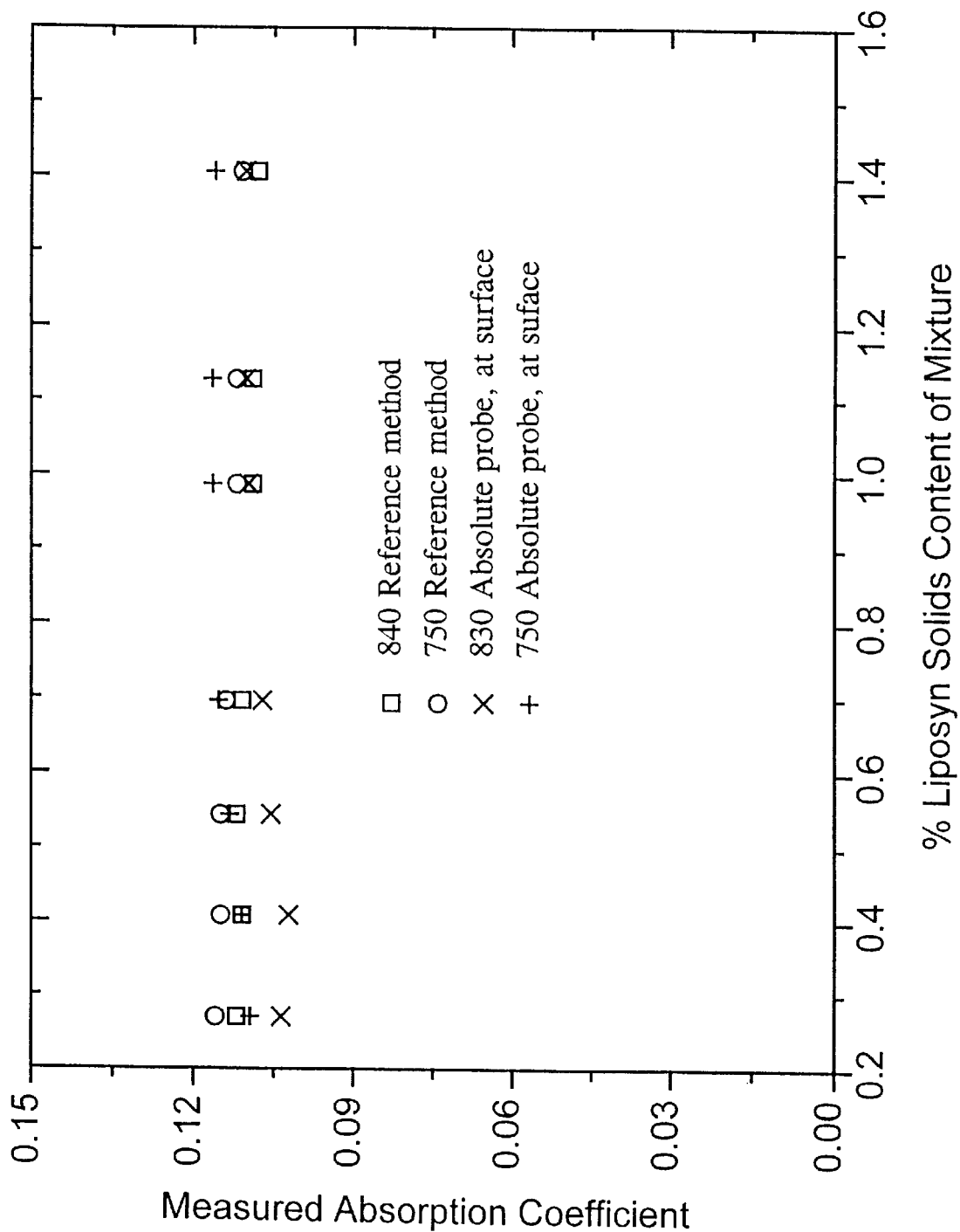
FIG. 7 is a graph showing measurement of the absorption coefficient at varying degrees of scattering.

In FIG. 7, the calculated, measured absorption coefficients for the respective absolute probe of FIG. 2 were compared with the reference probe method over a similarly varying Liposyn solids content, providing an increasing scattering as the solids content rises. The respective data at 750 nm. and 840 nm. for the IR radiation used is plotted. As before, the total content of the ink remains constant so that the concentration of the ink changes slightly only due to the small amount of dilution as more Liposyn is added.

The measuring system of FIG. 2 gave essentially the same absorption values within experimental error to the corresponding reference probe method, showing that absorption can be measured without the need for instrument calibration over large changes in the intensity of scattering.

While some of the results from the reference probe indicate small differences from the results of the absolute probe of FIG. 2, it is believed that the errors are primarily introduced by the approximations used in semi-infinite theory, and are not due to errors in the measured values of $UDC(x_1)\lambda/UDC(x_2)\lambda$; $UDC(x_1)\lambda/UDC(x_2)\lambda$; and $\Phi_U(x_1)\lambda - \Phi_U(x_2)\lambda$.

Similar results were obtained through the use and testing of the self-referencing system of FIG. 4.

The results of the above tests confirm that the probes of this invention and the method used allows the accurate and absolute measurement of absorption and scattering coefficients in homogeneous, highly scattering media. The technique is insensitive to changes in the intensity of the sources, even if the changes are differential among the sources. The technique is also insensitive to changes in the response of the detectors, changes in the coupling efficiency of fiber optic light guides, and even dirt on optical fibers used in the system. The improvement of this invention provides greatly increased resistance to drifts and changes in source or detector factors. Thus they are easier to use since they require no pre-measurement calibration, contrary to the prior art.

These new probes are preferably used with a frequency domain approach, but they are not limited to use with frequency domain instruments. It is possible to use these probes for "time domain" measurements with pulsed light sources. They can also be used to measure $U(x_1)\lambda/U(x_2)\lambda$ with steady state sources and detectors without modulation. The accurate measurements of $UDC(x_1)\lambda/UDC(x_2)\lambda$; $UDC(x_1)\lambda/UDC(x_2)\lambda$; and $\Phi_U(x_1)\lambda - \Phi_U(x_2)\lambda$ provided by the present invention can be useful in combination with mathematical methods other than those discussed here. For example, in U.S. Pat. No. 5,517,987 to Tsuchiya a method is described for the measurement of optical parameters using only DC measurement. Also, a non-frequency domain approach may be used similar to that illustrated in Komonu et al. U.S. Pat. No. 5,057,695.

The above has been offered for illustrative purposes only, and is not intended to limit the scope of the invention of this application, which is as defined in the claims below.

That which is claimed:

1. The method of determining parameters of a medium which comprises the steps of:

passing a first portion of light from a first light source through said medium to a first detector, and passing a second portion of light from said first light source through said medium to a second detector;

passing a third portion of light from a second light source through said medium to the second detector, the distance between said first light source and said first detector and the second light source and said second detector being substantially equal, and passing a fourth portion of light from said second light source through said medium to said first detector, the distance between said first light source and the second detector and the second light source and said first detector being substantially equal; and combining data received by said detectors in a manner that is substantially independent of: intensity of the light sources, sensitivity of the detectors, coupling efficiency of light from the light sources into said medium, and coupling efficiency of light from said medium to said detectors; and determining a parameter of said medium from said data, said light portions being of substantially identical wavelength.

2. The method of claim 1 in which data received by said detectors comprises the intensities of said light portions as a function of distances between detectors and light sources.

3. The method of claim 1 in which said method is repeated, sequentially using single members of a plurality of first light sources and a plurality of second light sources for improved data accuracy.

4. The method of claim 1 further comprising the step of respectively passing fifth and sixth portions of light from a third light source to said first and second detectors, said third light source being equidistantly positioned from said first and second detectors, to provide a reference light source for self-calibration of the detectors.

5. The method of claim 4 in which said method is repeated, sequentially using single members of a plurality of said third light sources for improved self-calibration accuracy.

6. The method of claim 1 in which said first and second detectors are parts of a single array detector.

7. The method of determining parameters of a highly scattering medium, which comprises the steps of sequentially:

passing a first modulated portion of light from a first light source through said highly scattering medium to a first detector, and passing a second modulated portion of light from said first light source through said highly scattering medium to a second detector;

passing a third modulated portion of light from a second light source through said highly scattering medium to said second detector, the distance between said first light source and said first detector and the second light source and said second detector being substantially equal, and passing a fourth modulated portion of light from said second light source through said highly scattering medium to said first detector, the distance between said first light source and the second detector and the second light source and said first detector being substantially equal;

said modulated portions of light being of substantially the same wavelength and each being modulated at the same frequency, said first and second light detectors being modulated at a second frequency that is different from said first frequency; and determining data points comprising a combination of data from said first and second detectors and determining a parameter of said medium from said data points.

8. The method of claim 7 in which said combined data is indicative of at least two of phase, AC, and DC components of signals from said detectors.

9. The method of claim 7 in which the parameter determined comprises at least one of an absorption coefficient, an index of refraction, and a scattering coefficient of said medium.

10. The method of claim 9 comprising the step of determining rate of change by distance in at least two of phase shift, ln DC, and ln AC components detected from the resultant signals derived from said light beams, and determining at least one of said absorption coefficient, index of refraction, and scattering coefficient of said medium from said rates of change.

11. The method of claim 10 comprising the step of determining an absolute concentration in said medium of at least one form of hemoglobin from said absorption coefficient, using said method twice with two different wavelengths of light.

12. The method of claim 11, comprising the step of determining the ratio of two forms of hemoglobin in a tissue.

13. The method of claim 10 comprising the step of determining a relative concentration of glucose in said medium from said scattering coefficient, multiplied by the index of refraction.

14. The method of claim 7 in which the step of determining the parameter of said medium from said data comprises the steps of combining the respective data received from the first and second detectors in a manner that is substantially independent of: intensity of the light sources, sensitivity of the first and second sensors, high frequency phase response of the light sources and sensors, coupling efficiency of light passing from the light sources to the highly scattering medium, and coupling efficiency of light passing from the highly scattering medium to the detectors, whereby calibration of the light sources and sensors is rendered unnecessary.

15. The method of claim 7 in which said method is repeated, sequentially using single members of a plurality of first light sources and sequentially using a plurality of second light sources for improved data accuracy.

16. The method of claim 7 further comprising the step of respectively passing fifth and sixth portions of light from a third light source to said first and second detectors, said third light source being equidistantly positioned from said first and second detectors, to provide a reference light source for self-calibration of the detectors.

17. The method of claim 16 in which said method is repeated, sequentially using single members of a plurality of said third light sources for improved self-calibration accuracy.

18. The method of claim 7 in which said first and second detectors are parts of a single array detector.

19. A self-referencing photosensor which comprises a probe having a face for contact with a medium for testing with a photosensing technique;

a controller electrically connected to said probe for receiving signals from said probe;

and a computer for receiving and processing signals from said controller responsive to the signals from said probe, and for converting said signals into data;

said probe having spaced first and second light sources positioned to emit light of substantially identical wavelength through apertures of said face, said probe also having spaced first and second detectors positioned to receive light from said medium passing through other apertures of said face;

said first light source having a spacing from said first detector which is equal to the spacing between said second light source and said second detector, said first light source having a spacing from said second detector which is equal to the spacing between said second light source and said first detector.

20. The self-referencing photosensor of claim 19 in which the face of said probe is adapted to be in contact with living tissue.

21. The self-referencing photosensor of claim 20 in which a plurality of said first light sources and a plurality of said second light sources are present.

22. The self-referencing photosensor of claim 19 in which a third light source is present to pass light through a third aperture in said face, said third light source being equidistantly positioned between said first and second detectors to provide a reference light source for self-calibration of the detectors.

* * * * *